(12) United States Patent
Kim et al.

(10) Patent No.: US 6,197,304 B1
(45) Date of Patent: Mar. 6, 2001

(54) **WHITENING COSMETICS CONTAINING SOLVENT-FRACTIONATED EXTRACTS OF *RAMULUS MORI* EXTRACT**

(75) Inventors: Jeong-Ha Kim, Seoul; Kang-Tae Lee, Chungcheongnam-do, both of (KR)

(73) Assignee: Coreana Cosemetics Co., Ltd. (KR)

( * ) Notice: Subject to any disclaimer, the term of this patent is extended or adjusted under 35 U.S.C. 154(b) by 0 days.

(21) Appl. No.: 08/987,149

(22) Filed: Dec. 8, 1997

(30) Foreign Application Priority Data

Sep. 12, 1997 (KR) .................................... 97-47259

(51) Int. Cl.$^7$ .................................... A61K 35/78
(52) U.S. Cl. ..................... 424/195.1; 424/401; 424/62
(58) Field of Search ................. 424/195.1, 401, 424/62

(56) References Cited

U.S. PATENT DOCUMENTS

| | | | | |
|---|---|---|---|---|
| 4,137,231 | * | 1/1979 | Murai et al. | 546/242 |
| 5,773,014 | * | 6/1998 | Perrier et al. | 424/401 |
| 5,872,254 | * | 2/1999 | Kim et al. | 546/242 |

FOREIGN PATENT DOCUMENTS

| | | | |
|---|---|---|---|
| 8150538 | * | 9/1983 | (JP) . |
| 9227353 | * | 9/1997 | (JP) . |

OTHER PUBLICATIONS

Heterocycles, vol. 15, No. 2, 1981; pp. 1531–1567; Taro Nomura, et al. "Prenylflavonoids from the root bark of the cultivated mulberry tree".

Cosmetics & Toiletries magazine; vol. 111, Oct. 1996; pp. 65–77; "Skin Lighteners".

Cosmetics & Toiletries magazine; vol. 107, Nov. 1992; pp. 61–68; Pawelek, et al.; "Ultraviolet Light and Pigmentation of the Skin".

Cosmetics & Toiletries magazine; vol. 112, Mar. 1997; pp59–62; Jang, et al.; "Melanogenesis Inhibitor from Paper Mulberry".

International Journal of Cosmetic Science 19, 000–000 (1997);pp.1–7; Lee, et al; "Biological screeneing of 100 plant extracts for cosmetic use (1): inhibitory activites of tyrosinase and DOPA auto–oxidation".

Chem. Pharm.Bull 25(3) pp. 529–532 (1977); "Kuwanon A,B,C and Oxydihydromorusin, Four New Flavones from the Root Bark of the Cultivated Mulberry Tree".

Heterocycles, vol. 14, No. 12, 1980; pp. 1943–1951; Taro Nomura, et al.; "Hypotensive constituent, kuwanon H, a new flavone derivative from the rootbark of the cultivated mulberry tree".

J. Soc. Cosmet. Chem., 42, 361–368 (Nov./Dec. 1991); Kazuhisa Maeda, et al.; "In vitro effectiveness of several whitening cosmetic components in human melanocytes".

Shin et al. Natural Product Sciences, vol. 3 (2), pp. 111–121, 1997.*

Choi et al. Foods Biotechnol. vol. 6 (1), pp. 44–49, abstract enclosed, 1997.*

Fukai et al. Chem. Pharm. Bull. vol. 33 (8), pp. 3195–3204, abstract enclosed, 1985.*

Nomura et al. Planta Med. vol. 47 (3), pp. 151–156, abstract enclosed, 1983.*

* cited by examiner

*Primary Examiner*—Christopher Tate
(74) *Attorney, Agent, or Firm*—Nields & Lemack

(57) ABSTRACT

The present invention relates to cosmetic products having whitening effect, which contains fractionated extracts of *Ramulus mori* (Marus) extracts. According to the present invention, an aqueous suspension of the *Ramulus mori* extracts, which have been obtained by extracting young twig of plants belonged to *Morus* Genus with water or an organic solvent, is solvent-fractionation-extracted to obtain a fractionated extracts of *Ramulus mori* extracts, which is then added to conventional skin-care cosmetics to give whitening cosmetics having excellent whitening effect.

1 Claim, 1 Drawing Sheet

WHITENING COSMETICS CONTAINING SOLVENT-FRACTIONATED EXTRACTS OF *RAMULUS MORI* EXTRACT

FIELD OF THE INVENTION

The present invention relates to cosmetic products having whitening effect, which contains solvent-fractionated extracts of *Ramulus mori* extracts that is extracted from young twig of plants belonged to *Morus* Genus.

PRIOR ARTS

In general, there are various reasons for the darkening of skin color. And the main reason is ultraviolet radiation. When skin is exposed to ultraviolet ray, melanin is synthesized in melanocytes, which is a kind of skin cells, and released to darken skin color. In the process of melanin synthesis in melanocytes, tyrosinase reacts on tyrosine, which is a substrate for tyrosinase, in the cell to yield Dopaquinone and it goes through spontaneous reaction and enzyme reaction to synthesize a copolymeric black pigment, melanin. Thus, to prevent darkening of skin color, it is most simple and general to inhibit a step of the process of generating melanin, to reduce the production of melanin.

For this reason, ascorbic acid, kojic acid, arbutin, hydroquinone or plant extracts like *Cortex mori* extracts have been conventionally used as whitening agents up to the present.

Among these, kojic acid forms a chelate with a copper ion at the active site of tyrosinase to inhibit the enzyme activity. Though it has high activity, it is not appropriate to be used in cosmetics because of its stability problem in the process of mixing in the cosmetic products.

Ascorbic acid cannot be properly used as a whitening agent because it has relatively low activity of inhibiting tyrosinase and low stability of the molecule itself.

Hydroquinone irritates the skin strongly, so that it is not used as a cosmetic material in these days because of its safety problem.

Most of plant extracts can reveal substantial inhibition effect on tyrosinase activity, only if they are used at a high concentration. When they are used at a low concentration, the inhibiting activity hardly occurs.

SUMMARY OF THE INVENTION

The present inventors have paid attention to these circumstances and performed intensive studies for finding a more excellent whitening agent which does not involve the problems of conventional whitening agents. As a result of searching for effective material having whitening activity among the natural plants of which the safety has been already proved as they have been used in herb remedies or folk remedies for a long time, the inventors found that the extracts of *Ramulus mori*, young twig of plants belonged to *Morus* Genus, showed excellent inhibition activity on tyrosinase. The result was filed as an invention with the Korea Industrial Property Office.

The object of the present invention is to provide whitening cosmetics containing solvent-fractionated extracts of *Ramulus mori* extracts.

In order to find a whitening agent having stronger effect of inhibiting tyrosinase, from *Ramulus mori* extracts, the inventors attempted solvent-fractionating of the extracts by the use of various organic solvents. As a result, they found that the solvent-fractionated extracts of *Ramulus mori* extracts has stronger effect of inhibiting tyrosinase activity than *Ramulus mori* extracts did, so that strongly inhibit the synthesis of melanin in melanocytes, to complete the invention.

DETAILED DESCRIPTION OF THE INVENTION

Figure 1:
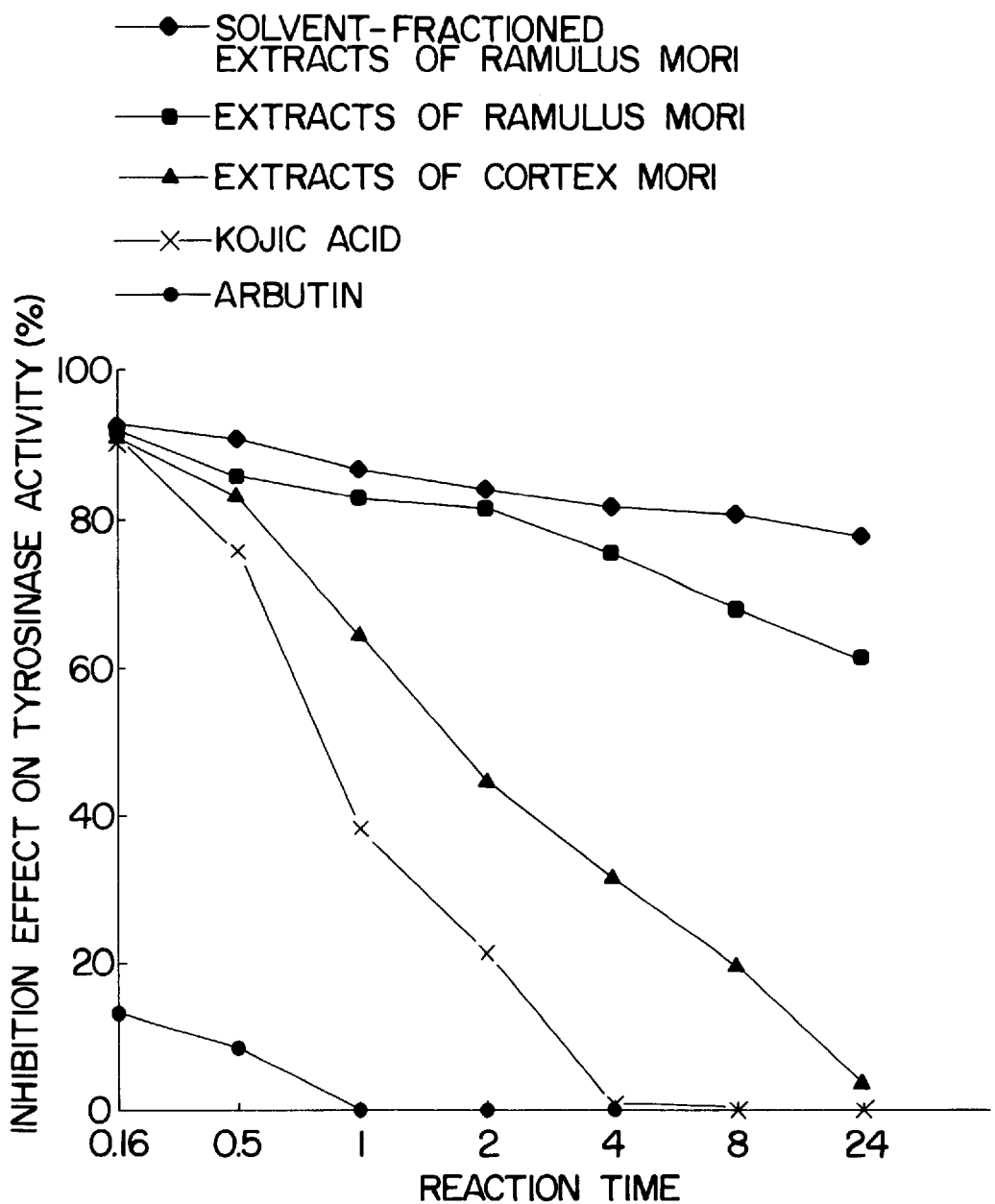
FIG. 1 shows the maintenance of the tyrosinase inhibition effect of the solvent-fractionated extracts of *Ramulus mori* extracts according to the present invention as compared to those of conventional whitening agents.

According to the present invention, an aqueous suspension of the *Ramulus mori* extracts, which have been obtained by extracting young twig of plants belonging to *Morus* Genus with water or an organic solvent, is solvent-fractionation-extracted to obtain a fractionated extracts of *Ramulus mori* extracts, which is then added to conventional skin-care cosmetics to give whitening cosmetics having excellent whitening effect.

*Morus* Genus includes *Morus alba*, Linne; *Morus alba* for. Pelldullus DIPPEL; *Morus bombycis*, Koidzumi; *Morus bombycis* var. Caudatifolia; *Morus bombycis* var. maritima KOIDZ; *Morus bombycis* for. Kase VYKEI; *Morus tiliaefolia*, Makino; and so on. These plants are tall trees of broad-leaved larch, widely distributed in Korean peninsula at a level of 500~1400 m of altitude and grow spontaneously around mountain villages or at the feet of mountains.

*Ramulus mori* is dried young twig of plants belonging to *Morus* Genus. The shape is like a long cylinder having side twigs sparsely. The size is not regular but the diameter is about 0.5~1.5 cm. The surface is greyish yellow or yellowish brown with lots of yellowish brown dot-like skin holes and minute seed-out, and with greyish white semicircular signs of leaves and yellowish brown axillary buds. The thickness of the cut piece is about 0.2~0.5 cm. The piece has relatively thin exodermis part and yellowish white woody part. The oblique line is radial and the head part is white or yellowish white. The gathering season is desirable between late spring and early summer. After removing the leaves, the twigs are cut in a length of 30~60 cm when they are still fresh, and dried under sunlight. *Ramulus mori* has somewhat bitter taste. And due to its activities of antiphlogistic, diuresis, invigorant, diaphoretic and alleviating paralysis, it has been used as a material of Chinese medicine from olden times.

The process for preparation of the solvent-fractionated extracts of *Ramulus mori* extracts used in the whitening cosmetics according to the present invention is as follows:

To a *Ramulus mori* extracts based on water or an organic solvent, water of one- to ten-fold amount of the dry weight of the extracts is added to form a suspension. The same amount of chloroform as that of water is added to the suspension to fractionate the extract. Among the two separated phases, the water-fractionated layer is isolated, and the same amount of ethyl acetate as that of water is added thereto, to separate the layer into two phases again. Then, ethyl acetate-fractionated layer is isolated and evaporated by using a rotary evaporator to dryness, to obtain the fractionated extracts of *Ramulus mori* extracts.

The process for preparing the *Ramulus mori* extracts prior to the fractionating process is as follows:

*Ramulus mori* is washed with purified water and cut into small pieces. Thereto, is added a solvent (such as water, absolute or aqueous lower alcohol containing 1~4 carbons, acetone, ethyl acetate, butyl acetate, chloroform or 1,3-butylene glycol) of one to ten weight folds of the dried pieces. The mixture is extracted by heating at 40~100° C. for 3~20 hours with an equipment of condenser to prevent the evaporation of active components, or by impregnating at 4~40° C. for 1~15 days. Then, the solvent of the extracts is completely removed to dryness by the use of a rotary evaporator.

The fractionated extracts of *Ramulus mori* extracts thus prepared is added to conventional skin-care cosmetics such as skin softener (skin lotion), nutrient emulsion (milk lotion), nutrient cream, massage cream, skin essence and facial pack. The amount of the fractionated extracts added is about 0.00001~5% (w/w), preferably 0.001~1% (w/w), based on the dry weight of each cosmetic product. In this manner, the cosmetic products having whitening effect can be prepared.

Preferred Embodiments of the Invention

Now, The present invention is described with reference to Examples, Comparative Examples and Experimental Examples. However, it should not be noted that the present invention is restricted to those examples.

EXAMPLE 1

*Ramulus mori* (1 kg), which had been washed with distilled water and dried, was added to 50% ethanol (5 L) and extracted at 4 to 40° C. for 5 days. The resultant material was filtered through 300 mesh filtering cloth and then the mixture was stood at 5~10° C. for 7~10 days for low-temperature aging. Then, the mixture was filtered through a filter paper of Whatman No. 5. The filtrate was concentrated to dryness by using rotary evaporator at 65° C. (dry weight: 48.96 g).

To the dry material, 480 ml of distilled water was added to form a suspension, to which 480 ml of chloroform added. Among the two separated phases, the water layer was isolated, and 480 ml of ethyl acetate was added thereto. The fractionated layer of ethyl acetate was isolated and concentrated at 70° C. by using a rotary evaporator to dryness to give the desired fractionated extracts (dry weight: 6.37 g).

EXAMPLE 2~12

*Ramulus mori* was extracted according to the same procedure as Example 1 and the results are recorded in Table 1.

TABLE 1

The experiment result of example 2~12

| Test material | Extract solvent of *ramulus mori* | The dry weight of final fractionated extract (g) |
| --- | --- | --- |
| Example 2 | 60% ethanol | 6.34 |
| Example 3 | 70% ethanol | 6.71 |
| Example 4 | 80% ethanol | 5.42 |
| Example 5 | 90% ethanol | 4.61 |
| Example 6 | 100% ethanol | 3.66 |
| Example 7 | 50% methanol | 8.72 |
| Example 8 | 60% methanol | 8.92 |
| Example 9 | 70% methanol | 9.51 |
| Example 10 | 80% methanol | 9.82 |
| Example 11 | 90% methanol | 9.53 |
| Example 12 | 100% methanol | 9.41 |

EXPERIMENTAL EXAMPLE 1

Inhibition effect of solvent-fractionated extracts of *Ramulus mori* extracts on tyrosinase activity The tyrosinase inhibition effect of each fractionated extracts of *Ramulus mori* extracts obtained from Examples 1~12 was determined.

A tyrosinase, commercially available one from Sigma Co. which had been separated from mushroom and purified, was used.

Each fractionated extracts obtained from Examples 1~12 was dissolved in 1,3-butylene glycol at a high concentration, and the solution was further diluted to an appropriate concentration with a buffer solution, to give an extracts sample.

Tyrosine solution (0.5 ml) was placed in a test tube and the extracts sample (0.5 ml) was added thereto. The test tube was stood in an incubator at 37° C. for 10 minutes, and then 200 U/ml tyrosinase (0.5 ml) was added thereto. The reaction was carried out at the same temperature for 10 minutes. As a control group, buffer solution (0.5 ml) was added instead of each fractionated extract. The reaction was quenched by placing the test tube containing the reaction mixture on ice. Absorbance was measured at a wavelength of 475 nm by using a spectrophotometer.

The inhibition effects of each fractionated extracts on tyrosinase activity was determined by the equation below:

Inhibition ratio of tyrosinase activity(%)=100−(100×Absorbance of each extract/Absorbance of control group)

The results are shown in Table 2.

TABLE 2

Inhibiting effect of fractionated extracts of *ramulus mori* extract on tyrosinase activity

| Test material | Concentration of final test (%, W/V) | Inhibition ratio of tyrosinase activity (%) |
| --- | --- | --- |
| Example 1 | 0.00050 | 96.8 |
| Example 2 | 0.00050 | 97.5 |
| Example 3 | 0.00050 | 99.4 |
| Example 4 | 0.00050 | 98.6 |
| Example 5 | 0.00050 | 98.7 |
| Example 6 | 0.00050 | 96.7 |
| Example 7 | 0.00050 | 98.9 |
| Example 8 | 0.00050 | 97.5 |
| Example 9 | 0.00050 | 97.9 |
| Example 10 | 0.00050 | 99.2 |
| Example 11 | 0.00050 | 98.6 |
| Example 12 | 0.00050 | 97.8 |

COMPARATIVE EXAMPLE 1

*Cortex mori* (1 kg) which had been washed with distilled water and dried was cut into pieces of 2–3 mm size, and extracted with 95% methanol (20 L) by stirring for 3 hours. The resultant extracts was filtered through a filter paper of Whatman No.6. The filtrate was concentrated to dryness by using a rotary evaporator at 65° C. [Fragrance Journal, 1990(6), pp59–66].

COMPARATIVE EXAMPLE 2–4

The procedures according to Example 3 were repeated but the *Ramulus mori* extracts before the solvent-fractionating extraction with chloroform (Comparative Example 2), kojic acid, a product of Sigma Co. (Comparative Example 3) and arbutin (Comparative Example 4) were used, respectively.

EXPERIMENTAL EXAMPLE 2

Comparison of tyrosinase inhibiting effect: Fractionated extracts of *Ramulus mori* extract vs. conventional whitening agents The fractionated extracts of *Ramulus mori* extracts prepared in Example 3 was used. inhibition effect on tyrosinase activity was measured according to the same procedure of Experimental Example 1. The inhibition effect of the fractionated extracts of *Ramulus mori* extracts was compared to those of conventional whitening agents, i. e., *Cortex mori* extracts, kojic acid, arbutin and the *Ramulus mori* extracts that had been invented by the present inventors.

The results are shown in Table 3.

TABLE 3

Tyrosinase inhibition effect of fractionated extracts of *ramulus mori* extracts and various whitening agents

| Whitening material | $IC_{50}$: μg/ml (Concentration required for 50% inhibition of tyrosinase activity) |
|---|---|
| Example 3 | 1.25 |
| Comparative 1 | 18.72 |
| Comparative 2 | 12.48 |
| Comparative 3 | 5.82 |
| Comparative 4 | 65.2 |

As can be shown from the above results, the fractionated extracts of *Ramulus mori* extracts showed much more excellent tyrosinase inhibition effect than conventional whitening agents such as *Cortex mori* extracts, kojic acid, and the like, did. Besides, the fractionated extracts of the present invention showed ten folds of the effect as compared to the *Ramulus mori* extracts before fractionating, that had been invented by the present inventors. Though kojic acid has relatively high whitening effect, it involves stability problems such as change of color, when it is incorporated in practical cosmetic products.

EXPERIMENTAL EXAMPLE 3
Comparison of maintenance of tyrosinase inhibition effect of the fractionated extracts of the present invention and *Cortex mori* extracts etc In order to examine whether the whitening agent exhibits maintained whitening effect, the reaction mixture containing the whitening agent was kept at 37° C. according to Experimental Example 1, and the inhibition effect on tyrosinase activity was measured over 24 hours.

The result shows that the fractionated extracts of *Ramulus mori* extracts exhibits quite excellent retentive whitening effect as compared to that of cortex mori extracts, kojic acid, arbutin, or the *Ramulus mori* extracts which had been invented by the present inventors (FIG. 1).

EXPERIMENTAL EXAMPLE 4
Effect of the fractionated extract of *Ramulus mori* extracts for melanin synthesis in melanocytes As melanocytes, commercially available B-16 melanoma (ATCC CRL 6323) cell line derived from mouse was used.

The melanoma cell line was inoculated in DMEM culture medium containing glucose (4.5 g/l), 10% serum and 1% antibiotic agent, and cultivated in a 50 ml T-flask at 37° C. After cultivating under a condition of 5% $CO_2$ for 24 hours, the culture solution was treated with 0.05% trypsin containing 0.02% EDTA to isolate cells, which was then inoculated in a 50 ml T-flask and cultivated for 48 hours. At this time, the number of cells was $4.857 \times 10^6$ cells/flask. A diluted solution of the fractionated extracts of *Ramulus mori* extracts in DMEM medium at a proper concentration was incorporated to the cultivated melanoma cells, and the mixture was cultivated at 37° C. for 5 days. After finishing cultivation, culture medium was thoroughly removed, and the residue was treated with 1 ml of saline-phosphate buffer solution (PBS) containing 0.02% EDTA and 0.05% trypsin to isolate cells, which were then centrifuged for 5 minutes to collect pure cells. The obtained cells were treated with a solution of 5% trichloroacetate (TCA), stirred, and centrifuged. Precipitated melanin was washed with saline-phosphate buffer solution, and treated with 1N NaOH to dissolve melanin therein. Absorbance at 475 nm was measured. Melanin concentration was determined from standard concentration curve of synthetic melanin (produced by Sigma Co.).

The results are shown in Table 4.

TABLE 4

Effect of the fractionated extracts of *ramulus mori* extracts for melanin synthesis in melanocytes

| Solvent-Fractionated extracts of *ramulus mori* extracts (μg/ml) | Melanin content (pg/cell) |
|---|---|
| no added | 3.91 |
| 10 | 1.58 |
| 20 | 1.35 |
| 50 | 1.01 |
| 100 | 0.58 |

The result shows that the fractionated extracts of *Ramulus mori* extracts is a strong whitening agent inhibiting melanin synthesis in melanocytes.

Formulation 1

An exemplary formula of a skin softener containing the fractionated extracts of *Ramulus mori* extracts is shown below. In the formula, the fractionated extracts of *Ramulus mori* extracts prepared in Example 3 was used.

| Component | Content (%, w/w) |
|---|---|
| fractionated extracts of *ramulus mori* | 0.1 |
| 1,3-butylene glycol | 6.0 |
| glycerin | 4.0 |
| oleyl alcohol | 0.1 |
| polysorbate 20 | 0.5 |
| ethanol | 15.0 |
| benzophenone-9 | 0.05 |
| preservatives, perfumes | small quantity |
| distilled water | residual quantity |
| Total | 100 |

Formulation 2

An exemplary formula of a milk lotion containing the fractionated extracts of *Ramulus mori* extracts is shown below. In the formula, the fractionated extracts of *Ramulus mori* extracts prepared in Example 3 was used.

| Component | Content (%, w/w) |
|---|---|
| fractionated extracts of *ramulus mori* | 0.1 |
| propylene glycol | 6.0 |
| glycerin | 4.0 |
| triethanol amine | 1.2 |
| tocopheryl acetate | 3.0 |
| liquid paraffin | 5.0 |
| squalane | 3.0 |
| macadamia nuts oil | 2.0 |
| polysorbate 60 | 1.5 |
| sorbitan sesquioleate | 1.0 |
| carboxyvinyl polymer | 1.0 |
| preservatives, perfumes | small quantity |
| distilled water | residual quantity |
| Total | 100 |

Formulation 3

An exemplary formula of a nutrient cream containing the fractionated extracts of *Ramulus mori* extracts is shown below. In the formula, the fractionated extracts of *Ramulus mori* extracts prepared in Example 3 was used.

| Component | Content (%, w/w) |
|---|---|
| fractionated extracts of *ramulus mori* | 0.1 |
| vaseline | 7.0 |
| liquid paraffin | 10.0 |
| wax | 2.0 |
| polysorbate 60 | 2.0 |
| solbitan sesquioleate | 2.5 |
| squalane | 3.0 |
| propylene glycol | 6.0 |
| glycerin | 4.0 |
| triethanol amine | 0.5 |
| carboxyvinyl polymer | 0.5 |
| tocopheryl acetate | 0.1 |
| preservatives, perfumes | small quantity |
| distilled water | residual quantity |
| Total | 100 |

Formulation 4

An exemplary formula of a massage cream containing the fractionated extracts of *Ramulus mori* extracts is shown below. In the formula, the fractionated extracts of *Ramulus mori* extracts prepared in Example 3 was used.

| Component | Content (%, w/w) |
|---|---|
| fractionated extracts of *ramulus mori* | 0.1 |
| propylene glycol | 6.0 |
| glycerin | 4.0 |
| triethanol amine | 0.5 |
| wax | 2.0 |
| tocopheryl acetate | 0.1 |
| polysorbate 60 | 3.0 |
| sorbitan sesquioleate | 2.5 |
| stearyl alcohol | 2.0 |
| liquid paraffin | 30.0 |
| carboxyvinyl polymer | 0.5 |
| preservatives, perfumes | small quantity |
| purified water | residual quantity |
| Total | 100 |

Formulation 5

An exemplary formula of a facial pack containing the fractionated extracts of *Ramulus mori* extracts is shown below. In the formula, the fractionated extracts of *Ramulus mori* extracts prepared in Example 3 was used.

| Component | Content (%, w/w) |
|---|---|
| fractionated extracts of *ramulus mori* | 0.1 |
| propylene glycol | 2.0 |
| glycerin | 4.0 |
| carboxyvinyl polymer | 0.3 |
| ethanol | 7.0 |
| PEG-40 hydrogenated castor oil | 0.8 |
| triethanol amine | 0.3 |
| preservatives, perfumes | small quantity |
| distilled water | residual quantity |
| Total | 100 |

EXPERIMENTAL EXAMPLE 5

Inhibition effect of color deposition

The back of a brown guinea pig was shaved and a part of 3×3 $cm^2$ was selected for serving the experiment. After attaching aluminum foil to the target part of the back so that ultraviolet ray might be irradiated only to the part, ultraviolet ray of 1.25 $mW/cm^2$ was irradiated for 6 minutes once a day by using SE lamp (produced by Toshiba, Japan) for 3 days. After irradiation, each cosmetic product of Formulation 1–5 described above was applied to the irradiated area twice a day during the time period of 3 weeks. The inhibition effect of color deposition was then determined by the naked eye.

The experimental results are shown in Table 5 below:

TABLE 5

Inhibiting effect of color deposition

| Test goods | The inhibiting effect of color deposition |
|---|---|
| Formulation 1 | little color deposition |
| Formulation 2 | little color deposition |
| Formulation 3 | little color deposition |
| Formulation 4 | weak color deposition |
| Formulation 5 | weak color deposition |

Color deposition was determined as 5 criteria of ① no color deposition, ② little color deposition, ③ weak color deposition, ④ medium color deposition, and ⑤ strong color deposition.

The solvent-fractionated extracts of *Ramulus mori* extracts according to the present invention exhibited much more intensive whitening effect than conventional whitening agents such as *Cortex mori* extracts, kojic acid and arbutin, and the *Ramulus mori* extracts, which had been developed by the present inventors did. The fractionated extracts exhibited very excellent retentive whitening effect than *Cortex mori* extracts did, a natural product originated from same plants of *Morus* Genus. In addition, the fractionated extracts has about 10 folds of inhibition effect on tyrosinase activity as compared to the *Ramulus mori* extracts which had been developed by the present inventors as well as excellent maintenance of the effect.

What is claimed is:

1. A fractionated extract of *Ramulus mori* prepared by:

extracting *Ramulus mori* with water or an organic solvent and evaporating said solvent to form a solid phase;

adding water to said solid phase in an amount of 1 to 10 times the dry weight of the solid phase to form a suspension;

adding to said suspension chloroform in the same amount as the added water to fractionate the suspension into two phases;

isolating the water-fractionated layer from the two phases, adding to the isolated water-fractionated layer, ethyl acetate in the same amount as the added water to separate the layer into two phases again;

isolating the ethyl acetate-fractionated layer, and evaporating, said isolated ethyl acetate-fractionated layer.

* * * * *